United States Patent [19]

Proksch et al.

[11] 4,045,176

[45] * Aug. 30, 1977

[54] PREPARATION OF OPTICALLY CLEAR SERUM

[76] Inventors: Gary J. Proksch, 586 W. 77th North Drive; Dean P. Bonderman, 1045 W. 77th South Drive, both of Indianapolis, Ind. 46260

[*] Notice: The portion of the term of this patent subsequent to May 11, 1993, has been disclaimed.

[21] Appl. No.: 671,175

[22] Filed: Mar. 29, 1976

Related U.S. Application Data

[63] Continuation-in-part of Ser. No. 586,569, June 13, 1975, Pat. No. 3,955,925, which is a continuation of Ser. No. 414,799, Nov. 12, 1973, abandoned.

[51] Int. Cl.² .................................... G01N 33/16
[52] U.S. Cl. .................. 23/230 B; 252/408; 260/112 B
[58] Field of Search ................. 23/230 B; 252/408; 260/112 B

[56] References Cited

U.S. PATENT DOCUMENTS

| | | | |
|---|---|---|---|
| 3,260,648 | 7/1966 | Fox | 23/230 B X |
| 3,274,062 | 9/1966 | Lou | 252/408 X |
| 3,682,835 | 8/1972 | Louderback | 23/230 B X |
| 3,764,556 | 10/1973 | Kuchmak et al. | 252/408 |
| 3,955,925 | 5/1976 | Proksch et al. | 23/230 B |

OTHER PUBLICATIONS

Jonas, J. Bio. Chem., vol. 247, No. 21, pp. 7767–7772, Nov. 1972.

*Primary Examiner*—Morris O. Wolk
*Assistant Examiner*—Arnold Turk
*Attorney, Agent, or Firm*—Woodard, Weikart, Emhardt & Naughton

[57] ABSTRACT

A stable optically clear serum is prepared for use in the preparation of standards and quality control reference material for the assay of human serum components. In one aspect of the present invention, high density lipoproteins isolated from human blood serum are added to substantially human serum to produce a standard or reference material. A second aspect of the present invention involves the addition of isolated, non-primate lipoproteins to substantially human serum. The serum prepared as disclosed has good optical clarity upon lyophilization and reconstitution with aqueous media. Alternatively, the isolated lipoproteins are added in an aqueous diluent to lyophilized human serum.

20 Claims, No Drawings

PREPARATION OF OPTICALLY CLEAR SERUM

CROSS-REFERENCE TO RELATED APPLICATIONS

This application is a continuation-in-part of our application having Ser. No. 586,569, filed June 13, 1975 and now issued as U.S. Pat. No. 3,955,925, which was a continuation of our original application having Ser. No. 414,799, filed on Nov. 12, 1973, now abandoned.

BACKGROUND OF THE INVENTION

1. Field of the Invention

This invention relates to the addition of isolated lipoproteins to substantially human serum to prepare a stable serum standard or reference having good optical clarity, particularly upon reconstitution from the lyophilized state.

2. Description of the Prior Art

The use of human serum standards or references in blood chemistry analysis is well known. It is frequently advantageous as a diagnostic aid to determine the levels of certain constituents of a patient's blood. This determination is made with the aid of human serum standards. These serum standards are commonly stored as a dry powder after lyophilization to be reconstituted at the time of use. Alternatively they may be frozen and thawed. It is desirable that the lyophilized human serum, when reconstituted with aqueous media, be stable and have substantial optical clarity to minimize interference with the analytical measurement of serum constituents.

Two important blood constituents are triglyceride and cholesterol. It is therefore desirable to prepare a human serum standard or reference containing triglyceride or cholesterol and having good optical clarity for use with analytical testing procedures. The serum should also be stable and easily reconstituted after storage in the lyophilized or frozen state. Further, certain processes for preparing a human serum standard involve the elimination of much or all of the triglyceride and cholesterol. It then becomes necessary to provide for the addition back of triglyceride or cholesterol if these are to be measured.

The source of the triglyceride and cholesterol for preparation of a human serum standard is important. The resulting substantially human serum must be stable and have good optical clarity, even after lyophilization and reconstitution. In U.S. Pat. No. 3,764,556, issued to Kuchmak et al. on Oct. 9, 1973, there is disclosed a technique for obtaining a triglyceride-rich fraction from egg yolk. The egg yolk fraction, however, must be used the same day that it is prepared since a precipitate is formed upon freezing and thawing. The Kuchmak et al. patent additionally discloses a procedure for obtaining a cholesterol-rich B-protein fraction from outdated human plasma for use in bovine and horse sera. It is believed that this is a low density lipoprotein fraction. The use of this protein fraction however, entails several disadvantages. First, there are certain dangers involved in that the procedure by which the cholesterol-rich fraction is obtained will also result in collection and concentration of any hepatitis virus which may be present in the plasma. Additionally, it has been found that serum turbidity will result upon lyophilization and reconstitution of the prepared cholesterol standard.

In general, present methods for preparing human serum standards provide a serium which displays turbidity upon lyophilization and reconstitution with aqueous media. Also, a process which utilizes human blood as a source of triglyceride or cholesterol to be added in preparing a serum standard will generally be expensive. Further, processes using triglycerides or cholesterol from primates can present risks of hepatitis.

SUMMARY OF THE INVENTION

One aspect of this invention relates to a method of preparing a human serum standard which displays minimal turbidity upon lyophilization and reconstitution, and which contains the major, normal human plasma constituents in desired concentrations. In one embodiment, isolated, high density human lipoproteins are added to substantially human serum having normal or reduced levels of cholesterol or triglyceride. In another embodiment of the invention, isolated, non-primate lipoproteins obtained from blood are utilized in the same manner. The lyophilized serum of this invention is particularly suitable as a base material for the preparation of standards and quality control reference material for the assay of human serum components.

In some embodiments of the invention, the lipid, cholesterol, and triglyceride levels of a lyophilized human serum are increased to desired levels by the reconstitution of the lyophilized serum with a diluent containing the isolated lipoproteins previously described.

It is an object of this invention to prepare a human blood serum which has normal or elevated triglyceride or cholesterol levels, and which is stable and has good optical clarity upon freezing and thawing or upon lyophilization and reconstitution with aqueous media.

It is a further object of this invention to provide a lyophilized human serum which has normal or elevated triglyceride or cholesterol levels, and which, upon reconstitution of the lyophilized serum, is readily soluble in water in a short period of time.

It is a still further object of this invention to provide a lyophilized product which has normal or elevated triglyceride or cholesterol levels, has good optical clarity upon reconstitution, and at the same time contains all the normal major blood plasma constituents.

It is an additional object of this invention to provide a diluent which contains triglyceride or cholesterol and which may be used to reconstitute lyophilized human blood serum to produce a stable and optically clear serum standard or reference.

A further object of this invention is to prepare a substantially human serum by the reconstitution of the lyophilized human serum with a diluent which contains isolated, non-primate lipoproteins.

It is an additional object of this invention to prepare an optically clear cholesterol standard using isolated, non-primate lipoproteins.

It is a still further object of this invention to prepare an optically clear triglyceride standard using isolated, non-primate lipoproteins.

These and other objects and advantages of this invention will become obvious by the following description of the preferred embodiment.

DESCRIPTION OF THE PREFERRED EMBODIMENT

Human serum or plasma contains four major classes of lipoproteins. Lipoproteins are a complex of a protein with a lipid. The four major classes are chylomicrons, very low density lipoproteins (pre-beta lipoproteins), low density lipoproteins (beta lipoproteins) and high density lipoproteins (alpha lipoproteins). The actual content varies for various samples with respect to certain physical and chemical parameters. A problem associated with lipoproteins is that their presence in serum tends to result in turbidity. This turbidity interferes with the use of standard turbidimetric or colorimetric measuring devices.

The actual starting substance of the disclosed procedure is blood plasma, which is defined as the liquid part of the blood containing fibrinogen. Normal human plasma is obtained from pooled blood. The pooled blood includes approximately equal volumes of the liquid portions of whole blood from not less than eight adult humans. Outdated, citrated whole blood, which is old whole blood to which citrate, phosphate and dextrose have been added, is preferable in view of its low cost.

From this pooled blood, normal human serum is derived. The serum is the clear, amber, alkaline fluid of the blood from which cellular elements have been removed by clotting. The serum contains the salts, soluble protein, and lipoproteins. The lipoproteins are rich in triglycerides and cholesterol.

In one embodiment of the invention, isolated, high density human lipoproteins are added to the human serum which is obtained as previously described. The provision that the high density human lipoproteins be isolated refers to the substantial removal therefrom of the low density lipoproteins and other constituents also present in human serum. It has been found that the low density lipoproteins contribute most to serum turbidity, as is disclosed in our patent application, Ser. No. 586,569, filed June 13, 1975, and now issued as U.S. Pat. No. 3,955,925. In contrast, the high density, alpha lipoproteins do not significantly contribute to serum turbidity, even after lyophilization and reconstitution of the serum with aqueous media. The high density human lipoproteins, then, are added to the otherwise substantially human serum to produce a stable serum standard or reference which has good optical clarity upon lyophilization and reconstitution.

Prior to addition of the isolated, high density human lipoproteins, the human serum may be processed to remove certain constituents. Preferably, those constituents which have been found to contribute to turbidity of the reconstituted serum are removed. In one embodiment of this invention, the triglyceride level of the human serum is reduced prior to addition of the isolated, high density human lipoproteins. The isolated, high density human lipoproteins are then added to the processed, substantially human serum to achieve the desired concentration. The resultant serum standard is stable and displays good optical clarity upon reconstitution from the lyophilized state.

Another aspect of the present invention involves the addition of isolated, non-primate lipoproteins to the human serum obtained as previously described. It has been found that the lipoproteins of non-primates do not significantly contribute to turbidity of the resultant serum. Since the ratio of high density lipoproteins to low density lipoproteins in non-primate serum is normally naturally higher than in primate serum it is ordinarily not necessary that the high-density lipoproteins of the non-primates be exclusively used, but the low density lipoproteins may be included without substantial adverse effect. It therefore is not necessary that the high and low density lipoproteins for the non-primates first be separated as is required when human lipoproteins are being used. The present invention does contemplate, however, that the lipoproteins obtained from the non-primate serum will be substantially isolated from the serum and the other serum constituents. This is in direct contrast to the embodiment previously described in which the high density lipoproteins obtained from human serum are to be isolated additionally from the low density lipoproteins. It may, of course, be desirable to add other constituents to the human serum standard or reference to bring the levels of those particular constituents to the desired point, but this is not required by the present invention.

The serum prepared utilizing the isolated non-primate lipoproteins retains its clarity upon lyophilization and reconstitution with water. Upon reconstitution of the dry powder, the material rapidly solubilizes, generally within 30 minutes, and is optically clear.

The lipoproteins of various non-primates have been found to produce by the present method serum standards which result in varying degrees of accuracy in subsequent measurements of the added constituents. Bovine lipoproteins are most preferred because they are readily and inexpensively available, and produce a serum which measures accurately as a standard or reference material. In addition, it should be noted that the bovine and other non-primate lipoproteins, do not present the potential for the presence of the hepatitis virus, which may be concentrated in the high density lipoprotein fraction of human serum.

The non-primate lipoproteins are added to human serum to produce a serum standard having standard or elevated levels of triglyceride, cholesterol or both. As in the case of human lipoproteins, the non-primate lipoproteins exist either as high or low density species, and the amount of triglyceride or cholesterol associated with the various species will differ. Thus, triglyceride-containing or cholesterol-containing lipoproteins obtained, for example, from bovine serum, may be added to the human serum to obtain a standard or reference material having the desired level of either or both of these constituents.

A further embodiment of the present invention involves the addition of the isolated, non-primate lipoproteins to human serum which has a reduced level of particular constituents. Human serum having a significantly reduced level of triglycerides, but containing high density lipoproteins, will retain optical clarity upon lyophilization and reconstitution. In addition, non-primate lipoproteins, and preferably bovine lipoproteins, may be added to the serum to produce a standard or reference material having normal or elevated levels of lipids, cholesterol, or triglycerides. The resulting serum, when lyophilized according to known techniques, remains stable for several months at 5° C. The lyophilized serum is easily reconstituted to form an optically clear serum. Similarly, non-primate lipoproteins, preferably bovine lipoproteins, are added to human serum having all normally present lipoproteins and chylomicrons removed. The resulting serum is stable in lyophilized form and readily reconstitutes to an optically clear serum.

In still another embodiment of the present invention, the isolated, non-primate lipoproteins or isolated, high density human lipoproteins are added as a diluent to lyophilized, substantially human serum to produce an optically clear and stable serum standard. The lyophilized human serum has normal or reduced levels of lipids, triglyceride or cholesterol. The isolated lipoproteins are added to the lyophilized human serum as an aqueous solution. The concentration of the lipids, triglyceride and cholesterol in the resulting serum standard or reference is controlled by the concentration of the lipoproteins in the aqueous diluent and by the amount of diluent added to the lyopholized human serum.

EXAMPLE 1

A normal 1000 ml. pooled human blood plasma sample was obtained. A bovine blood lipoprotein extract was added to bring the cholesterol level to the desired level.

The bovine lipoprotein extract was obtained in the following manner. To bovine serum, calcium chloride was added to achieve a 0.05 molar Ca cation concentration. Dextran sulfate was added to achieve a 0.5 g/l concentration. The resulting precipitate comprised mainly low-density lipoproteins and was removed and saved. To the remaining serum, additional calcium chloride was added to achieve a concentration of 0.25 molar. Additional dextran sulfate was added to achieve a concentration of 2.5 g/l. The resulting precipitate was removed and consisted of essentially a complex of dextran sulfate and high-density lipoprotein and a minor amount of low-density lipoprotein.

The second precipitated complex of bovine lipoprotein and dextran sulfate was dissolved in 50 ml. of 10% sodium bicarbonate solution. Any precipitates which formed were removed and discarded. The supernatant was dialyzed against water and then 1% $BaCl_2$. Any precipitates which formed were removed and discarded and the supernatant was again dialyzed against water. This final purified bovine lipoprotein solution, which had a concentration of 20 g/l cholesterol, was added to the human serum in an amount sufficient to achieve a cholesterol level of 4.0 g/l in human serum. The resultant serum provided an excellent serum standard for elevated cholesterol levels, and displayed excellent optical clarity.

A portion of the prepared serum was freeze-dried to a powdered form and stored at 5° C for 40 weeks. After storage, distilled water was added to reconstitute the serum. The serum, 10 minutes after reconstitution with water, was optically clear.

EXAMPLE 2

The procedure of Example 1 was followed exactly except the first bovine precipitate fraction, mainly low density lipoproteins, was additionally processed and added prior to adding the final lipoprotein fraction. The first precipitate fraction was added to achieve an elevated level of triglyceride in the serum standard. This first precipitated complex of bovine lipoprotein and dextran sulfate is dissolved in 10 ml. of 10% sodium bicarbonate solution. Any precipitates which form are removed and discarded. The supernatant is then dialyzed against water and then against 1% $BaCl_2$. Any precipitates which form are removed and discarded and the solution if again dialyzed against water. After storage exactly as in Example I, acceptable clarity results were obtained, although the results were not nearly as good as the results obtained with Example 1.

EXAMPLE 3-4

A normal 1000 ml. pooled human blood plasma sample was obtained. A bovine blood lipoprotein extract was added to bring the cholesterol level to the desired level.

The bovine lipoprotein extract was obtained according to the technique of Jonas as described in the Journal of Biological Chemistry, Volume 247, pages 7767 et seq. Briefly, the bovine serum was allowed to clot at room temperature and was centrifuged at 60,000 rpm for about 24 hours. A first fraction of primarily low density lipoproteins and chylomicrons was then removed from the top of the solution and saved. A further top portion was removed and discarded and contained a mixture of low and high density material. The remaining solution was centrifuged under the same conditions and a second fraction comprising primarily high density lipoproteins was drawn off the top.

The second fraction was added to the human serum in an amount sufficient to achieve a cholesterol level of 4.0 g/l in human serum. The resultant serum displayed excellent optical clarity both initially and after lyophilization and reconstitution with water. A serum was also prepared by adding both of the lipoprotein fractions to human serum. The clarity of this latter serum was acceptable, though not as good as for the serum to which only the first fraction was added.

EXAMPLES 5-8

A normal 1000 ml. pooled human blood sample was obtained. A bovine blood lipoprotein extract was added to bring the cholesterol level to the desired level.

The bovine lipoprotein extract was obtained according to the procedure of Oncley et al. as disclosed in the Journal of the American Chemical Society, Volume 79, pages 4666 et seq. Briefly, a 0.5% (w/v) solution of dextran sulfate solution was added with stirring to bovine serum. A lipoprotein-dextran sulfate precipitate was allowed to form and was separated by centrifugation. The precipitate was then suspended in a 2.0 M sodium chloride solution and was ultracentrifuged. The liquid separated into four distinct layers.

Portions of the top three layers were individually and collectively dialyzed against water and 1% $BaCl_2$ and added to portions of the human serum. The top layer contained the lowest density lipoproteins and successively lower layers contained progressively higher density fractions of lipoproteins. The serums produced by combination of the human serum with either one or all of the three layers displayed good optical clarity, although the serums containing the lower density bovine lipoproteins displayed some cloudiness not present with the other serums.

EXAMPLE 9-32

The procedures of Examples 1-8 were followed exactly except the lipoprotein fractions were obtained from horse, chicken and dog serums. The cholesterol concentrations of the overall extracts for the horse, chicken and dog serums were 10.0, 8.5 and 9.5 g/l, respectively.

Human serum standards made by the addition to human serum of exclusively the primarily high density liproprotein extracts displayed excellent clarity both initially and after lyophilization and reconstitution. Standards prepared by addition to human serum of the primarily low density lipoprotein extracts were initially clear, but were cloudy after lyophilization and reconstitution. The serum standards prepared with the combined high and low density lipoprotein extracts of horse serum displayed good optical clarity both initially and after lyophilization and reconstitution. Standards prepared similarly with extracts from dog and chicken serums were clear initially, but became cloudy upon reconstitution from the lyophilized state.

EXAMPLE 33

The procedure of Example 1 was followed exactly except that the primarily high-density lipoprotein extract was obtained from human serum. Excellent clarity results were obtained even after lyophilization and reconstitution when the human high-density lipoprotein extract was used.

EXAMPLE 34

A normal 1000 ml. pooled human blood plasma sample was obtained. The plasma was then prepared as described in my U.S. Pat. application, Ser. No. 586,569, filed June 13, 1975, now issued as U.S. Pat. No. 3,955,925. Calcium chloride was added to the plasma to achieve a 0.06 molar concentration of calcium cation in the plasma. The pH was adjusted to 7.4 using 1.5 ml. to 6N NaOH. The mixture was then heated to 37° C and 1 ml. of topical bovine thrombin (1000 NIH units per ml.) was added. The plasma was allowed to clot and the serum was then expressed from the clot. Dextran sulfate was added to the serum to achieve a concentration of 0.5 g/l. A flocculent lipoprotein-complex precipitate was formed at pH 7.4. The precipitate was subsequently removed and discarded, and the resulting supernatant serum was optically clear. The excess calcium was removed by dialysis, treatment with oxalate or ion exchange techniques.

The serum was freeze-dried to a powdered form and stored at 5° C for 40 weeks. After storage, distilled water was added to reconstitute the serum. The serum, 10 minutes after reconstitution with water, was optically clear.

EXAMPLES 35–68

The procedures of Examples 1–33 were followed with a single exception. The bovine lipoprotein extracts were added not to the normal human serum, but to serum having a reduced cholesterol-triglyceride level by the process of Example 34. After storage exactly as in Example I, exceptionally good clarity results were obtained except for those serums for which less favorable results were noted in EXAMPLES 9–32.

EXAMPLES 69–101

Lipoprotein extracts were prepared in the manners described in EXAMPLES 1–32. The extracts were then diluted 1 to 5 with distilled water under sterile conditions. The diluted extracts were added as a diluent to reconstitute lyophilized human serum. The resulting serums displayed excellent clarity except for those serums prepared by addition of the diluted, primarily low density extracts of dog and chicken serums.

While there have been described above the principles of this invention in connection with specific examples, it is to be clearly understood that this description is made only by way of example and not as a limitation in the scope of the invention.

What is claimed is:

1. A substantially human serum for use as a standard or reference material is assaying human blood, said human serum being improved by containing in addition to essentially all normal human serum components, isolated non-primate, animal lipoproteins which contain cholesterol.

2. A lyophilized form of the serum of claim 1.

3. The serum of claim 1 in which the non-primate, animal lipoproteins comprise primarily high density lipoproteins.

4. The serum of claim 1 in which said human serum contains a sufficient amount of the animal lipoproteins to achieve a level of cholesterol in the substantially human serum of 4.0 grams per liter.

5. The serum of claim 1 in which the non-primate, animal lipoproteins comprise bovine lipoproteins obtained from bovine serum.

6. A lyophilized form of the serum of claim 5.

7. A substantially human serum for use as a standard or reference material in assaying human blood, said human serum being improved by containing in addition to essentially all normal human serum components, isolated non-primate, animal lipoproteins which contain mainly low density lipoproteins.

8. A lyophilized form of the serum of claim 7.

9. The serum of claim 5 in which the non-primate, animal lipoproteins comprise bovine lipoproteins obtained from bovine serum.

10. A lyophilized substantially human serum for use as a standard or reference material in assaying human blood, said human serum having its triglyceride level significantly reduced but containing high density lipoproteins and essentially all other serum components normally present in human serum.

11. The serum of claim 10 which contains non-primate, animal lipoproteins.

12. The serum of claim 11 in which the non-primate, animal lipoproteins comprise bovine lipoproteins obtained from bovine serum.

13. A substantially human serum for use as a standard or reference material in assaying human blood, said human serum having normally present lipoproteins removed, but containing non-primate, animal lipoproteins.

14. A lyophilized form of the serum of claim 13.

15. The serum of claim 13 in which the non-primate animal lipoproteins comprise bovine lipoproteins obtained from bovine serum.

16. A method of preparing a substantially human serum for use as a standard or reference material which comprises the addition of isolated high density lipoproteins to human serum.

17. The method of claim 16 which additionally includes the step of lyophilizing the mixture produced.

18. A method of preparing a substantially human serum for use as a standard or reference material which comprises the addition of isolated, high density lipoproteins to lyophilized human serum.

19. A method of preparing a substantially human serum for use as a standard or reference material which comprises the addition of non-primate, animal lipoproteins to lyophilized human serum.

20. The method of claim 19 in which the non-primate, animal lipoproteins comprise bovine lipoproteins obtained from bovine serum.

* * * * *